(12) United States Patent
Stegmann

(10) Patent No.: US 7,175,595 B1
(45) Date of Patent: Feb. 13, 2007

(54) METHOD FOR ADJUSTING OF CONTROLLING THE DIET AND/OR A PERSON'S CONSUMPTION

(76) Inventor: Heiner Stegmann, Friedrich-Ebert-Anlage 25, 63450 Hanau (DE)

( * ) Notice: Subject to any disclaimer, the term of this patent is extended or adjusted under 35 U.S.C. 154(b) by 166 days.

(21) Appl. No.: 10/019,446

(22) PCT Filed: Jun. 29, 2000

(86) PCT No.: PCT/EP00/06060

§ 371 (c)(1),
(2), (4) Date: Dec. 31, 2001

(87) PCT Pub. No.: WO01/00091

PCT Pub. Date: Jan. 4, 2001

(30) Foreign Application Priority Data

Jun. 29, 1999 (DE) ................. 199 29 508
Oct. 14, 1999 (DE) ................. 199 49 479

(51) Int. Cl.
*A61B 5/00* (2006.01)
(52) U.S. Cl. ...................... 600/300; 128/920
(58) Field of Classification Search ........ 600/300–301; 128/898, 920, 921; 482/8–9; 434/127; 708/131, 708/133
See application file for complete search history.

(56) References Cited

U.S. PATENT DOCUMENTS

| 4,951,197 | A | | 8/1990 | Mellinger | |
|---|---|---|---|---|---|
| 5,081,991 | A | * | 1/1992 | Chance | ............... 482/8 |
| 5,839,901 | A | * | 11/1998 | Karkanen | ........... 434/127 |
| 6,478,736 | B1 | * | 11/2002 | Mault | ............ 600/300 |

OTHER PUBLICATIONS

Kornstad et al., "Low Calorie diet, exercise and hypertension. 2 pilot studies using a protein-rich low-calorie diet powder", PubMed Abstract, Tidsskr Nor Laegeforen. Dec. 10, 1991; 111(30):3627-9.*
XP002150591 "Noninvasive Detection of the Anaerobic Threshold During Computer-Controlled Exercise Testing", Talbot et al, Medical & Biological Engineering & Computing, vol. 23, No. 6, Nov. 1985, pp. 579-584.

* cited by examiner

*Primary Examiner*—Max F. Hindenburg
*Assistant Examiner*—Michael C Astorino
(74) *Attorney, Agent, or Firm*—Dennison, Schultz & MacDonald

(57) ABSTRACT

The invention relates to a method for adjusting or controlling the diet and/or consumption of carbohydrates and/or fats and/or proteins of a person who is subjected to a certain physical strain taking into consideration his/her individual performance potential to be determined.

4 Claims, No Drawings

METHOD FOR ADJUSTING OF CONTROLLING THE DIET AND/OR A PERSON'S CONSUMPTION

This application is a filing under 35 USC 371 of PCT/EP00/06060, filed Jun. 29, 2000.

BACKGROUND OF THE INVENTION

The invention relates to a method for adjusting or controlling the nutrition and/or consumption of carbohydrates and/or fats and/or proteins of a person who is subjected to a certain physical stress.

The invention relates in particular to a method for determining necessary nutrition and/or nutritional therapeutic substances for controlling a person's nutrition by indirectly determining his/her individual carbohydrate, fat and protein shares in the provision of his/her energy level through standardized stress tests and the controlled consumption of such shares while taking the results that were determined in the standardized stress tests into consideration.

Carbohydrates, fats and proteins are substrates, which are metabolized in the muscles for energy production, e.g. ATP production. During the transition from a resting position to a state of strong stress, great changes occur in the muscle's metabolism. Due to the increased need for energy, especially the rate of substrate conversion increases drastically.

In this context it is of great importance that in the muscle under stress also the conversion rate ratios of the individual substrates to each other change tremendously, i.e. the percentage of carbohydrate, fat and protein conversion in the overall substrate conversion process is regulated in the muscle as a function upon stress.

SUMMARY OF THE INVENTION

The invention is based on the problem of developing a method of the above-described kind in such a way that with simple measures a reliable adjustment or control of a person's nutrition and/or consumption as a function upon the relevant stress in relation to the carbohydrate and/or fat and/or protein percentages occurs, wherein especially among people who are exposed to great stress such as athletes or sick or elderly people a controlled adjustment of the supplied carbohydrates and/or fats and/or proteins or the consumption occurs. According to the invention, the problem is largely resolved by the fact that for the control and/or adjustment of the person's nutrition and/or consumption his/her performance capacity is determined by determining characteristic performance capacity parameters and that as a function upon the determined performance capacity the carbohydrate and/or fat and/or protein percentage requirements and/or consumption by the person is determined, by basing the calculation on the stress that is decisive for nutrition and/or consumption.

DETAILED DESCRIPTION OF THE

According to the invention it is suggested that, for controlling and/or adjusting the nutrition and/or consumption of nutrients in a person, his/her performance capacity is determined by determining characteristic performance capacity parameters and that his/her need for and/or consumption of carbohydrates and/or fats and/or proteins in his/her food is determined as a function upon the determined performance capacity of the person, basing the calculation on stress-specific substrate mixture ratios that are decisive for nutrition and/or consumption. Substrate mixture ratios should be interpreted as the carbohydrate and/or fat and/or protein percentages.

In particular the invention provides for the fact that for the purpose of determining the performance capacity of the person the heart rate and/or blood pressure and/or ergospirometric parameters and/or lactate concentration in the blood is measured or determined as a function upon the stress.

In a preferred embodiment of the invention, a scaling to a lactate accumulation rate $\Delta A$ occurs for the purpose of determining the performance capacity above the individual anaerobic threshold, wherein in particular the lactate accumulation rate $\Delta A$ is used as a basis for determining the nutrition and/or consumption of the person in relation to his/her protein percentage from glucogenic amino acids.

A method for determining the lactate accumulation rate $\Delta A$ is characterized by the following procedural steps:

measuring the time-dependent lactate concentrate change beyond the individual anaerobic threshold, adjusting a measurement curve to measurement values gained this way, in which the lactate concentrate in relation to time is entered, determining a first gradient in the measurement curve at a time $t_{IAT}$ that corresponds to the individual anaerobic threshold, determining at least one additional gradient in the measurement curve at a time $t_x$ with $t_x > t_{IAT}$ subtracting the second gradient from the first gradient to determine a difference, which represents the lactate accumulation rate $\Delta A$.

In order to be able to provide information about the stress-specific regulation of the substrate metabolism of test subjects, initially the performance capacity stress ability of these test subjects must be determined with a standardized test, which allows the possibility of estimating the aerobic/anaerobic transition. Such tests can be conducted with various methods.

For determination of the performance capacity, different stress types can be applied such as running tests, swimming tests, stepping tests, ergometry methods, e.g. bicycle, treadmill, rowing ergometry with gradual and/or continuous stress increase, performed with or without breaks.

Alternatively, the following parameters, which can be measured or deduced from the measurement parameters, can be used to determine the performance capacity:

heart rate (HF) under stress
HF max (with stress)
HF submax (anaerobic-aerobic transition: Conconi test)
HF related performance (physical working capacity)
HF related oxygen intake
blood pressure (RR)
stress blood pressure (systolic)
blood pressure amplitude
ergospirometric parameters
minute volume (AMV)
oxygen intake ($VO_2$)
maximum $VO_2$ ($VO_2$ max)
respiration rate (AF)
carbon dioxide emission ($VCO_2$)
respiratory equivalent (AÄ=AMV/$VO_2$)
oxygen pulse ($VO_2$/HF)
acid/base status, pH value
respiratory quotient (RQ)
ventilatory equivalent for $CO_2$ and $O_2$
anaerobic threshold (according to Wasserman)
individual anaerobic threshold (according to Stegmann)
lactate concentrate in blood IATs according to Stegmann ΔA according to Stegmann Lactate threshold concepts with fixed lactate concentration and gradients model-related parameters deduced from the lactate curve parameters deduced from lactate curve and ergospirometric data.

The most exact method however is the determination of the lactate performance curve in the graduated test with determination of the individual anaerobic threshold according to Stegmann (IATs) as well as the IATs-adjusted lactate accumulation rate ΔA.

The lactate performance curve of a human being can be changed only very slowly through training and/or lifestyle. From its course, information can therefore be deducted about the performance and training behavior of a human being over an extended period of time, i.e. the lactate performance curve of a person can be interpreted as "medium-term memory" of his/her lifestyle.

In relation to the IATs and the ΔA value of a test subject and with consideration of the above-described explanations, the following general statements with regard to the carbohydrate, fat and protein consumption of a test subject under stress can be made ($\Delta A_{max}$=largest determinable ΔA value in a test subject)

| Stress Intensity | Duration | CH | Fat | Protein |
|---|---|---|---|---|
| Start and graduated start | very short [s] | + | ++ | +++ |
| > IATs, ΔA -> $\Delta A_{max}$ | short [≦ min] | + | ++ | +++ |
| > IATs, ΔA << $\Delta A_{max}$ | short [6–10 min] | ++ | ++ | ++ |
| ≦ IATs | short [> 2 min] | ++ | ++ | + |
| ≦ IATs | medium [< 60 min] | ++ | ++ | + |
| ≦ IATs | long [> 60 min] | ++ | +++ | ++ |

The relative stress intensities and stress duration periods, to which a person is exposed e.g. in his/her daily life or during sports activities, therefore regulate the ratios of carbohydrate, fat and protein percentages in his/her nutrient consumption. These ratios are shown as a rough outline in the above table. These results can be applied directly for the development of required formula nutrition or nutritional therapeutics that have been adjusted to the individual performance capacity so as to avoid nutritional deficiencies.

When adjusted to the individual anaerobic threshold and/or the adjusted lactate accumulation rate ΔA, the need for carbohydrate, fat and protein percentages as a function upon stress intensity and stress duration—in accordance with the table—offers the possibility to expose a test subject to stress in such a controlled manner that carbohydrates and/or fat percentages are used in the desired scope.

The method according to the invention thus represents a connection between knowledge about stress-specific substrate consumption, i.e. carbohydrate, fat and protein consumption of a person, and the possibility to evaluate this specificity based on performance tests and to deduce individual nutritional recommendations or control the substrate consumption through appropriate selection of training modes.

The invention claimed is:

1. Method for adjusting nutrition in a person subjected to physical stress, comprising the steps of:

determining performance capacity of the person by determining individual anaerobic threshold of the person and measuring lactate accumulation rate ΔA at and above the individual anaerobic threshold;

determining a stress state of the person in relation to the measured individual anaerobic threshold and measured lactate accumulation rate ΔA; and regulating at least one of fat, protein and carbohydrate consumption of the person as a function of the determined stress state, individual anaerobic threshold and lactate accumulation rate, wherein the step of determining the lactate accumulation rate ΔA comprises the steps of:

measuring time-dependent lactate concentration change beyond the individual anaerobic threshold, plotting a measurement curve of measured lactate concentration in relation to time, determining a first gradient in the measurement curve at a time $t_{IAT}$ that corresponds to the individual anaerobic threshold, determining at least one second gradient in the measurement curve at a time $t_x$ with $t_x > t_{IAT}$; and subtracting the second gradient from the first gradient to determine a difference, which represents the lactate accumulation rate ΔA.

2. Method according to claim 1, wherein the stress occurs in a person over an extended period of time below the determined individual anaerobic threshold, and the fat and the carbohydrate percentage of the nutrition are adjusted comparatively higher than the protein percentage.

3. Method according to claim 1, wherein the stress occurs with a lactate accumulation rate ΔA approaching $\Delta A_{max}$, and the protein percentage of the nutrition is adjusted up to several times as with stress at ΔA=0.

4. Method according to claim 1, wherein the performance capacity is determined under a stress selected from the group consisting of a running test, a swimming test, a stepping test and ergometry with graduated or continuous stress increase with and without breaks.

* * * * *